United States Patent
Kyriatsoulis et al.

(10) Patent No.: US 6,635,485 B1
(45) Date of Patent: Oct. 21, 2003

(54) STABILIZATION OF CALIBRATORS CONTAINING CYTOKERATIN

(75) Inventors: Apostolos Kyriatsoulis, Weilheim (DE); Gunter Pappert, Starnberg (DE); Ellen Moessner, Buehlerzell (DE); Norbert Franken, Starnberg (DE); Michael Rottmann, Weilheim (DE); Heinz Bodenmueller, Tutzing (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/857,002

(22) PCT Filed: Dec. 2, 1999

(86) PCT No.: PCT/EP99/09407

§ 371 (c)(1),
(2), (4) Date: Oct. 24, 2001

(87) PCT Pub. No.: WO00/33085

PCT Pub. Date: Jun. 8, 2000

(30) Foreign Application Priority Data

Dec. 3, 1998 (DE) .......................... 198 55 819

(51) Int. Cl.⁷ .............................. G01N 31/00
(52) U.S. Cl. ............... 436/8; 435/5; 435/7.92; 435/7.9; 435/7.1; 436/518; 436/18; 436/17; 436/16
(58) Field of Search ............ 435/5, 7.1, 7.9, 435/7.92; 436/8, 16, 17, 18, 518

(56) References Cited

U.S. PATENT DOCUMENTS

| 4,301,028 A | 11/1981 | Bartl et al. ............... 252/408 |
| 4,409,334 A | 10/1983 | Lill et al. ................... 436/8 |
| 5,288,614 A | 2/1994 | Bodenmuller et al. ..... 435/7.23 |
| 5,656,289 A | * 8/1997 | Cho et al. ................ 424/455 |
| 5,858,683 A | * 1/1999 | Keesee et al. ............. 435/7.1 |

FOREIGN PATENT DOCUMENTS

| DE | 3019612 A1 | 11/1981 | ............ C12N/9/74 |
| DE | 300491 A7 | 6/1992 | .......... G01N/33/96 |
| EP | 0014349 A1 | 8/1980 | .......... G01N/33/86 |
| WO | WO91/01497 | 2/1991 | .......... G01N/31/00 |
| WO | WO91/10139 | 7/1991 | ......... G01N/33/574 |
| WO | WO 91/19196 | * 12/1991 | ................. 33/543 |

OTHER PUBLICATIONS

Japanese Abstracts, Kawada Hidenobu, et al., "Stabilizer of Cytokeratin and Immunoassay of Cytokeratin Using the Same" 19970912, (1pp).

* cited by examiner

Primary Examiner—Long V. Le
Assistant Examiner—Deborah A. Davis
(74) Attorney, Agent, or Firm—Brinks Hofer Gilson & Lione

(57) ABSTRACT

The invention concerns calibrators or calibration solutions which are based on a human serum matrix and which are used in a method for detecting cytokeratin, a process for producing them, a method for stabilizing cytokeratin and an immunological method for detecting cytokeratin in a sample.

24 Claims, No Drawings

STABILIZATION OF CALIBRATORS CONTAINING CYTOKERATIN

FIELD OF THE INVENTION

The present invention concerns calibrators or calibration solutions which are based on a human serum matrix and which are used in a method for detecting cytokeratin, a process for producing them, a method for stabilizing cytokeratin in human serum and an immunological method for detecting cytokeratin in a sample.

BACKGROUND OF THE INVENTION

Immunological detection methods have become very important in diagnostics. They are characterized by a high specificity and sensitivity and hence they are also very suitable for detecting low concentrations of analytes in biological fluids. Immunological detection methods are of major importance particularly in the fields of infectious diseases, fertility and thyroid diagnostics, for metabolic diseases and for diagnosing tumour diseases. At present carcino-embryonic antigen (CEA), alpha-fetoprotein (AFP), prostate-specific antigen (PSA) and cytokeratins (CK) are for example among the most significant tumour markers.

Human cytokeratins are building blocks of the intermediary filaments which are the major components of the cytoskeleton of epithelial cells. More than 19 cytokeratins are known of which cytokeratins 1 to 8 are referred to as basic cytokeratins and cytokeratins 9 to 19 are referred to as acidic cytokeratins. The cytokeratins can aggregate in the cell to form tetramers. A tetramer consists of two basic and two acidic cytokeratin molecules in each case. Linear aggregation of tetramers results in the formation of filaments. Intact cytokeratin molecules are water-insoluble as integral components of the intermediary filaments of epithelial cells. The complexity and composition of the cytokeratins differs in the various epithelial tissues i.e. epithelial cells have cytokeratin compositions that are typical for the respective tissue. The soluble fragments of cytokeratin 19 (CK 19) which are also referred to as CYFRA 21-1 are particularly relevant for tumour diagnostics. A concentration of CYFRA 21-1 that is increased in comparison to healthy persons indicates the presence of a tumour disease. Increased values have previously been found in the following tumours: bronchial carcinoma, ovarial cancer, cervix carcinoma, bladder carcinoma and in tumours of the head and neck. The main indication for CYFRA 21-1 is to monitor non-small cell bronchial carcinomas.

A method for detecting CK 19 by a sandwich ELISA technique is described for example in EP-A-0 460 190. In this method the body fluid sample to be examined is incubated with at least two receptors R1 and R2, R1 and R2 being monoclonal antibodies which each detect different epitopes of CK 19. One of the antibodies is labelled with biotin and the other carries a different label. The sandwich complex comprising R1, CK 19 and R2 binds to a solid phase coated with streptavidin. After separating the solid from the liquid phase, the label is measured in one of the two phases and preferably in the solid phase. The tumour marker CK 19 can be detected in the sample on the basis of the signal that is obtained.

When carrying out such a test it is important that the measured value that is obtained can be at least classified qualitatively as positive (tumour marker is present) or as negative (the tumour marker is not present). This applies especially to the classification of measurement data that are obtained by means of automated systems. It is often also desirable or necessary to quantify the concentrations of tumour marker. Hence the test system must be calibrated with reagents that contain a defined concentration of analyte before carrying out the measurements. These defined reagents are referred to in the following as calibrators. The terms calibration solution, calibration standard, standard solution or control are used synonymously for the term calibrator.

An important requirement for a calibrator is high stability. On the one hand it is necessary to ensure the accuracy of the test, an essentially 100% recovery of the analyte in the calibrator and a good signal to noise ratio. On the other hand a reliable reproducibility of the result of the determination must be guaranteed over a long time period. Hence calibrators must be insensitive to their environmental conditions over a time period of several weeks i.e. to temperature, direct solar radiation on the laboratory bench, pH value, buffer conditions etc. If the conditions are unfavourable there is a risk of hydrolysis, proteolysis or denaturation of the calibrator. The use of a calibrator that is no longer intact would lead to erroneous measurements.

Many tests are carried out in serum samples. In order to ensure comparability of the measurements, the calibrator should therefore also be based on a serum matrix. The more sensitive the measuring system, the larger the differences in measurement will become due to the jump in the matrix between sample and calibrator. It has been shown that cytokeratin is unstable in a serum matrix. When a calibrator containing cytokeratin is stored in a liquid state, the cytokeratin is destroyed and denatured and hence such a calibrator cannot be used for a long time period.

Hence in the past the serum matrix was replaced by an artificial matrix the composition of which mimics that of serum. The artificial matrix is generally based on a buffer to which various salts and proteins (for example bovine serum albumin) are added in order to simulate as closely as possible the natural human serum environment with regard to salt and protein concentration as well as pH value. Although this enabled the analyte cytokeratin to be stabilized in the calibrator, a disadvantage of this procedure is that comparability is not optimal especially with sensitive measuring systems since the underlying matrix of the samples is human serum. There is therefore a jump in the matrix. This can lead to measuring errors with samples in the low measuring range near to the cut-off value. In extreme cases this could lead to a disparity between the value determined for a positive cytokeratin signal using the calibrator based on an artificial matrix and the value determined for a human serum sample even when the cytokeratin analyte is present in each case at a comparable concentration.

DETAILED DESCRIPTION OF THE PRESENTLY PREFERRED EMBODIMENTS

Hence the object was to provide a calibrator for methods for detecting cytokeratin which is based on a serum matrix and preferably a human serum matrix and which is stable for a period of at least several weeks even under unfavourable ambient conditions.

The object is achieved by a calibrator whose essential components are serum, preferably human serum, cytokeratin and aprotinin. It surprisingly turned out that the addition of the protease inhibitor aprotinin can effectively stabilize cytokeratin. Consequently it is possible to provide a calibrator for cytokeratin detection methods which is manufactured on a natural serum matrix basis and in particular is based on a human serum matrix. This avoids a jump in the matrix when measuring the actual serum samples.

Furthermore it turned out that the calibrator according to the invention has a long shelf life and temperature stability. Thus the recovery rate for the cytokeratin analyte dissolved in the calibrator, preferably CK 19, is almost 100% in a sandwich immunoassay after stressing the lyophilised calibrator for three weeks at 30 to 40° C. Thus the cytokeratin is not destroyed and is still immunologically recognized by the antibodies used in the test even after the time-temperature stress. The measured concentrations of cytokeratin in the various calibrators measured at the start of the stability test essentially correspond to the concentrations after the stress test. Hence the stability and precision of the calibrator according to the invention is comparable with the stability of a corresponding calibrator based on an artificial matrix. Even when the calibrator is stored at 2 to 8° C. in a liquid or reconstituted form which corresponds to the usual storage temperature of reagents in a refrigerator, a cytokeratin recovery of almost 100% was found even after 10 weeks. This means that the calibrator according to the invention can still be used after long storage in a refrigerator without qualitative or quantitative impairment.

The protease inhibitor aprotinin is of major importance for the substantially improved stability of the calibrator according to the invention. Other protease inhibitors proved to be ineffective. Aprotinin is a commercially available polypeptide which is composed of 58 amino acids. It has an inhibitory effect on the coagulation factors XIIa, XIa and VIIIa as well as on plasmin and plasmin activators, as well as trypsin, chymotrypsin and kallikrein. surprisingly other known protease inhibitors have proven to be unsuitable for stabilizing the calibrator. Experiments with other substances such as detergents and salts did not result in the desired stabilizing effect.

Aprotinin is preferably used at a concentration of at least 10 mg/l in the calibrator. The maximum possible concentration is that which interferes with the test or at which turbidity starts due to the lack of solubility. Concentrations between 25 and 40 mg/l are particularly preferred.

The calibrator can either be prepared in a liquid form or as a lyophilisate. In order to prepare the lyophilisate, all liquid and solid components are firstly mixed together or dissolved and subsequently lyophilised. The lyophilisate is then finally used as a reconstituted solution i.e. it is dissolved again in liquid. Distilled water is usually used for the reconstitution i.e. to redissolve the lyophilisate since this does not add undesired ions to the calibrator and in particular does not change the salt concentrations. The amount of water depends on the desired cytokeratin concentration or on the desired fill volume.

The calibrator according to the invention can additionally also contain conventional substances known to a person skilled in the art such as salts or additional preservatives. For example N-methyliso-thiazolone and oxypyrion are preferably added at the usual concentrations of about 1 mg/l.

The calibrator according to the invention can preferably be stored in a lyophilized form at 4° C. for several months without loss of quality. It can be stored for a period of up to 36 months at 4° C. The calibrator can be stored in a reconstituted form for several months at 4° C.

Cytokeratin-free human serum is preferably used as the serum. This can be obtained by affinity chromatographic processing or a serum is used which is free of cytokeratin from the beginning which has to be determined by appropriate screening methods.

The invention additionally concerns a process for producing the calibrator according to the invention. The calibrator is preferably produced by the following steps
  a) mixing serum with aprotinin
  b) filtering the solution
  c) dissolving the cytokeratin in water
  d) mixing the solution from step b) with the dissolved cytokeratin from step c)
  e) lyophilizing the solutions from d)
  f) dissolving the lyophilisate in water before use.

If necessary the pH value can be adjusted in step d) to pH 7 to 8, preferably 7.2.

A further subject matter of the invention is also a process for producing stabilized cytokeratin which is characterized in that the protease inhibitor aprotinin is added to the preferably purified cytokeratin. The stabilized cytokeratin produced in this manner is preferably used in a calibrator.

Another subject matter of the invention is the use of aprotinin to stabilize cytokeratin and in particular CK 19.

A subject matter of the invention is also a method for stabilizing cytokeratin in serum, preferably human serum which is characterized in that aprotinin, preferably at a concentration of at least 10 mg/l, is added to the serum.

A further subject matter of the invention is an immunological method for determining cytokeratin in a sample and in particular to determine CK 19. The method is characterized in that the signal determined for the sample is compared with the signal which is obtained with the aid of the calibrator according to the invention, the calibrator being measured using the same method as for the sample.

Such a method for determining cytokeratin and preferably for determining CK 19 and the calibrator is preferably carried out using the following steps:
  a) reacting the sample with a first binding partner that is specific for cytokeratin and carries a group capable of binding to a solid phase which can be used to bind it to a solid phase,
  b) reacting this solution with a further binding partner which carries a label
  c) binding the immune complex that is formed to a solid phase, whereby the solid phase can already be present in step a)
  d) separating the solid from the liquid phase
  e) detecting the label in one of the two phases.
  f) comparing the measured values for the calibrator with the value for the sample and quantification.

The method can also be carried out as a competitive test by methods known to a person skilled in the art.

The binding partners are preferably monoclonal or polyclonal antibodies or fragments thereof such as $F(ab')_2$, Fab' or Fab fragments which can specifically immunologically recognize and bind cytokeratin and in particular CK 19. The antibodies are produced by methods familiar to a person skilled in the art. Antibodies are also included which have been produced by modifying the antibodies for example by genetic engineering. The term antibody includes all aforementioned meanings for binding partners.

The first specific binding partner for cytokeratin can either be directly bound to the solid phase or the binding to the solid phase occurs indirectly via a specific binding system. The direct binding of this binding partner to the solid phase occurs according to methods known to a person skilled in the art. If the binding is indirect via a specific binding system, then the first binding partner is a conjugate comprising an antibody to cytokeratin and one reaction partner of a specific binding system. In this case a specific binding system is understood as two partners that can specifically react one another. The binding capability can be based on an immunological reaction or on another specific reaction. A combination of biotin and avidin or biotin and streptavidin is preferably used as the specific binding system. Other preferred combinations are biotin and antibiotin, hapten and anti-hapten, Fc fragment of an antibody and antibody to this Fc fragment or carbohydrate and lectin. One of the reaction partners of the specific binding pair is then a part of the conjugate.

The other reaction partner of the specific binding system for the first binding partner is present as a coating on the solid phase. The other reaction partner of the specific binding system can be bound to an insoluble carrier material by conventional methods known to a person skilled in the art. In this case a covalent as well as an adsorptive binding is suitable.

Suitable solid phases are test tubes or microtitre plates made of polystyrene or similar plastics whose inner surface is coated with a reaction partner of the specific binding system. Other suitable and particularly preferred solid phases are particulate substances such as latex particles, magnetic particles, molecular sieve materials, glass beads, plastic tubes etc. Porous layer-like carriers such as paper can also be used as carriers. Magnetic particles, so-called beads, are particularly preferably used and are in turn coated with the appropriate binding partner of the specific binding system described above. In order to carry out the detection reaction, these microparticles can then be separated from the liquid phase after completion of the test reaction for example by filtration, centrifugation or by a magnet in the case of magnetic particles.

The specific binding reactions between the antibodies to cytokeratin and cytokeratin can be detected in various ways. Usually one binding partner of the specific binding reaction is labelled. Common labels are chromogens, fluorophores, substances capable of chemiluminescence or electrochemiluminescence, radioisotopes, haptens, enzyme labels or substances which can in turn form a specific binding pair such as biotin/streptavidin.

All biological fluids familiar to a person skilled in the art can be used as samples to carry out the method for the detection of cytokeratin. Body fluids are preferably used as the sample such as whole blood, blood serum, blood plasma, urine or saliva, particularly preferably blood serum.

The invention is further elucidated by the following examples.

EXAMPLE 1

Production of the Calibrator According to the Invention

The stated identification numbers (Id No.) refer to catalogue numbers from Boehringer Mannheim GmbH, Germany. In order to prepare 1 litre CK calibrator (CK concentration 40 ng/ml) the following are mixed together.
A: commercial human serum made cytokeratin-free by affinity chromatography
B: 34 mg aprotinin, Id.No: 0236632-001
C: 1 g N-methylisothiazolone HCL, Id.No: 1085901-105
D: 1 g oxypyrion, Id.No: 1085913-05
E: 7.31 g cytokeratin from a stock solution having a concentration of 0.05 µg/ml containing 941 g A+B+C+D The human cytokeratin Cyfra 21-1 that was used corresponds to the cytokeratin from the human cell line MCF-7 of the Cyfra 21-1 CalSet, calibration set from the Elecsys® CYFRA 21-1 immunoassay from Boehringer Mannheim GmbH, Germany Id.No: 1820974.

EXAMPLE 2

Stressing the Calibrator at 35° C.

The procedure is according to the Elecsys® Cyfra 21-1 method from Boehringer Mannheim GmbH (Id.No. 1 820 966). The Elecsys® test procedure is based on the biotin/streptavidin technology. The test principle is a 1-step sandwich ELISA using two antibodies that recognize different epitopes on the analyte (cytokeratin). The solid phase comprises magnetic latex beads coated with streptavidin to which a biotinylated antibody that is specific for cytokeratin binds. The bound tumour marker is detected after separation of the solid from the liquid phase by measuring the electrochemiluminescence which is generated by a second specific antibody for cytokeratin that is labelled with a ruthenium complex.

The following raw materials are used:
R1 (first antibody, biotinylated Fab fragment)
  MAB<CK19>M-KS19.1-Fab(DE)-Bi(DDS); concentration 1.5 µg/ml
R2 (second antibody, ruthenylated IgG):
  MAB<CK19>M-BM19.21-IgG-BPRU); concentration 2.1 µg/ml 90 µl R1 and 90 µl R2 are incubated together with streptavidin-coated magnetic beads according to the instructions of the manufacturer of the Elecsys®2010 instrument from Boehringer Mannheim GmbH, Germany and measured.

The freshly dissolved calibrator according to the invention containing cytokeratin was compared to a calibrator according to the invention that was stressed for 3 weeks in a lyophilised state at 35° C. and subsequently reconstituted. The results are shown in table 1.

TABLE 1

(example 2):
Human matrix master calibrators, freshly dissolved and after a three week stress at 35° C.

| | freshly dissolved | | after a 3 week stress at 35° C. | |
|---|---|---|---|---|
| MC | conc. (ng/ml) | recovery (%) | conc. (ng/ml) | recovery (%) comp. to fresh |
| 1 | 0.0 | / | 0.0 | / |
| 2 | 0.88 | 100 | 0.87 | 99 |
| 3 | 7.57 | 100 | 7.10 | 94 |
| 4 | 18.13 | 100 | 17.19 | 95 |
| 5 | 60.85 | 100 | 57.62 | 95 |
| 6 | 125 | 100 | 119 | 95 |
| 7 | 302 | 100 | 296 | 98 |
| 8 | 450 | 100 | 430 | 96 |
| 9 | 613 | 100 | 604 | 96 |

MC: master calibrator: calibrator that is used to calibrate a new reagent lot before dispatch
rec: recovery The table shows that the stressed calibrator also has a good and almost 100% recovery. The deviation is in each case less than 10% (largest deviation 6%). Hence the calibrator according to the invention is stable towards a high temperature over a long time period and yields reliable calibration values even after stress. Even if the calibrator is accidentally stored incorrectly it can be used further without reservation and without impairment of quality.

EXAMPLE 3

Long-term Stress of the Calibrator at 4° C. (Liquid)

A comparison was made between freshly dissolved calibrator and calibrator which was stored before the measurement in a liquid reconstituted form at 4° C for 10 weeks. The measurements are carried out as described in example 2. The results are shown in table 2.

TABLE 2

(example 3):
Human matrix standard, freshly dissolved
and after a 10 week storage at 4° C.

| Standard | freshly dissolved conc. (ng/ml) | recovery (%) | after 10 week storage at 4° C. conc. (ng/ml) | recovery (%) comp. to fresh |
|---|---|---|---|---|
| A | 0.20 | / | 0.44 | / |
| B | 3.33 | 100 | 3.13 | 94 |
| C | 8.00 | 100 | 7.85 | 98 |
| D | 18.84 | 100 | 17.81 | 95 |
| E | 54.52 | 100 | 51.68 | 95 |
| F | 100.89 | 100 | 95.53 | 95 |

The calibrator according to the invention also exhibits good results in a liquid form with regard to signal recovery and concentration recovery after a stress for 10 weeks at 4° C.

EXAMPLE 4

Long-term Stability of the Calibrator: 24 Months at 4° C./24 Months −20° C.

A comparison was made between the calibrator which was stored before the measurement for 24 months at 4° C. and the calibrator which was stored for 24 months at −20° C. (each as a lyophilisate). The procedure is as described in example 2. The results are shown in table 3.

TABLE 3

(example 4)
Human matrix calibrators after 24 months
storage at −20° C. and +4° C.

| standard | 24 months at −20° C. conc. (ng/ml) | recovery (%) | 24 months at +4° C. conc. (ng/ml) | recovery (%) relative to fresh |
|---|---|---|---|---|
| MC1 | 0.0 | / | 0.0 | / |
| MC2 | 3.71 | 100 | 3.85 | 104 |
| MC3 | 9.01 | 100 | 9.04 | 100 |
| MC4 | 40.11 | 100 | 39.82 | 99 |
| MC5 | 394.8 | 100 | 395.0 | 100 |

There is a good recovery in both stress methods. Calibrator containing cytokeratin can be stored without reservation in a lyophilized form over time periods of several years at +4° C. or −20° C. without significant impairment to the quality.

EXAMPLE 5

Comparison of Measured Values of Tumour Marker Controls: Calibration of the Measuring Instrument on an Artificial Matrix and Human Serum Basis The Elecsys® measuring instrument is calibrated before carrying out the measurements with the calibrator containing cytokeratin based on an artificial matrix and subsequently the tumour marker controls are measured on the basis of these calibration values. The values found for this measurement are set at 100% recovery according to definition. Subsequently the same instrument is calibrated with the human serum based calibrator according to the invention and again the tumour marker controls are measured on the basis of these calibration values. The results are shown in table 4.

The tumour marker controls TMC I or II and PCT I or II are based on processed human serum and contain the cytokeratin Cyfra 21-1 with target values for two concentration ranges (I and II) in addition to other tumour markers such as PSA and AFP.

TABLE 4

(example 5)
Comparison between tumour marker controls;
cytokeratin calibration based on an
artificial matrix compared to a
human serum based calibration

| tumour marker control | calibration with calibrator based on an artificial matrix | | calibration with calibrator based on human serum | |
|---|---|---|---|---|
| | conc. (ng/ml) | recovery (%) | conc. (ng/ml) | recovery (%) |
| TMCI | 4.63 | 100 | 5.07 | 110 |
| TMCII | 28.5 | 100 | 29.8 | 105 |
| PCTI | 4.99 | 100 | 5.23 | 105 |
| PCTII | 30.7 | 100 | 31.7 | 103 |

It can be seen that the deviations between measurements of tumour marker controls based on calibrations using the calibrators based on an artificial or human matrix are no more than 10%. The values obtained for the tumour marker controls are thus independent of the calibrator used to calibrate the instrument. The calibrator based on human serum can thus replace the calibrator based on an artificial matrix.

What is claimed is:

1. A calibrator for use in the detection of cytokeratins, the calibrator comprising:
   a serum, a known concentration of cytokeratin, and aprotinin.

2. The calibrator of claim 1, wherein said serum comprises a natural serum.

3. The calibrator of claim 2, wherein said natural serum comprises human serum.

4. The calibrator of claim 3, wherein said human serum is substantially cytokeratin-free.

5. The calibrator of claim 1, wherein said aprotinin is present in a concentration of at least 10 mg/l.

6. The calibrator of claim 1, wherein said aprotinin is present in a concentration from about 25 mg/l to about 40 mg/l.

7. The calibrator of claim 1, wherein said cytokeratin comprises CK 19.

8. The calibrator of claim 1, further comprising a preservative.

9. The calibrator of claim 8, wherein said preservative comprises n-methylisothiazolone.

10. The calibrator of claim 8, wherein said preservative comprises oxypyrion.

11. The calibrator of claim 1, wherein the calibrator is in a liquid form.

12. The calibrator of claim 1, wherein the calibrator is a lyophilisate.

13. The calibrator of claim 1, wherein the calibrator is stable for three weeks at 30° C. to 40° C.

14. The calibrator of claim 1, wherein the calibrator is stable for at least ten weeks at 2° C. to 8° C.

15. The calibrator of claim 1, wherein the calibrator is stable for up to 36 months at 4° C.

16. A method for stabilizing a cytokeratin calibrator wherein said calibrator contains a serum and a known concentration of cytokeratin, said method comprising adding aprotinin to the calibrator.

17. The method of claim 16, wherein the resulting calibrator has an aprotinin concentration of least 10 mg/l.

18. The calibrator of claim 16, wherein the resulting calibrator has an aprotinin concentration from about 25 mg/l to about 40 mg/l.

19. A process for producing a cytokeratin calibrator, the process comprising:

mixing a serum with aprotinin to form a solution;

dissolving a known concentration of cytokeratin in water;

mixing said solution and said dissolved cytokeratin to form the cytokeratin calibrator.

20. The process of claim 19, further comprising lyophilizing said calibrator.

21. A method for determining the concentration of cytokeratin in a sample, the method comprising:

measuring a first value relating to the concentration of cytokeratin in the sample;

measuring a second value relating to the concentration of cytokeratin in a calibrator using the same methodology used to measure the first value, the calibrator comprising a serum, a known concentration of cytokeratin and aprotinin; and comparing the measured first value to the measured second value to determine the concentration of cytokeratin in the sample.

22. The method of claim 21, wherein the cytokeratin in said sample and said calibrator comprises CK 19.

23. The method of claim 21, wherein said calibrator comprises at least 10 mg/l of aprotinin.

24. The calibrator of claim 21, wherein said calibrator comprises about 25 mg/l to about 40 mg/l of aprotinin.

* * * * *